(12) United States Patent
Dacquay et al.

(10) Patent No.: US 8,876,751 B2
(45) Date of Patent: Nov. 4, 2014

(54) PHACOEMULSIFICATION HANDPIECE PRESSURE BOOSTER

(75) Inventors: Bruno Dacquay, Irvine, CA (US); Robert J. Sanchez, Jr., Oceanside, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 904 days.

(21) Appl. No.: 12/536,539

(22) Filed: Aug. 6, 2009

(65) Prior Publication Data
US 2011/0034864 A1    Feb. 10, 2011

(51) Int. Cl.
*A61M 1/00*    (2006.01)

(52) U.S. Cl.
USPC ............. 604/28; 604/118; 604/119; 604/120; 604/121

(58) Field of Classification Search
USPC ............................................ 604/28, 118–121
See application file for complete search history.

(56) References Cited

U.S. PATENT DOCUMENTS

| | | | |
|---|---|---|---|
| 3,882,872 A * | 5/1975 | Douvas et al. ............... | 606/107 |
| 3,930,505 A * | 1/1976 | Wallach ....................... | 604/22 |
| 4,496,342 A | 1/1985 | Banko | |
| 4,904,238 A | 2/1990 | Williams | |
| 5,106,367 A | 4/1992 | Ureche et al. | |
| 5,167,620 A | 12/1992 | Ureche et al. | |
| 5,429,601 A | 7/1995 | Conley et al. | |
| 5,476,448 A | 12/1995 | Urich | |
| 5,515,930 A | 5/1996 | Glaser | |
| 5,712,543 A | 1/1998 | Sjostrom | |
| 5,782,634 A | 7/1998 | Lingenhole et al. | |
| 5,827,218 A | 10/1998 | Nguyen et al. | |
| 5,989,212 A | 11/1999 | Sussman et al. | |
| 5,997,499 A | 12/1999 | Sussman et al. | |
| 6,042,586 A | 3/2000 | Kawano et al. | |
| 6,080,128 A | 6/2000 | Sussman et al. | |
| 6,110,162 A | 8/2000 | Sussman et al. | |
| 6,179,805 B1 | 1/2001 | Sussman et al. | |
| 6,196,989 B1 | 3/2001 | Padget et al. | |
| 6,206,848 B1 | 3/2001 | Sussman et al. | |
| 6,216,573 B1 * | 4/2001 | Moutafis et al. ............. | 83/177 |

(Continued)

FOREIGN PATENT DOCUMENTS

WO    WO 2008/157674 A1    12/2008
WO    WO 2011/016953 A1    2/2011

OTHER PUBLICATIONS

Kishimoto, Makoto, MD, Opesaver-Super Irrigation System, Techniques in Ophthalmology, 2006, 6 pages, vol. 4, Issue 1, Lippincott Williams & Wilkins, Shiga, Japan.

(Continued)

*Primary Examiner* — Edelmira Bosques

(57) ABSTRACT

In various embodiments, a handpiece may include an irrigation line coupled to an adjacent line reservoir with a piston configured to move within the adjacent line reservoir to increase an irrigation pressure in the irrigation line near a surgical site. In some embodiments, a sensor may be used to detect an occlusion break in the aspiration line and information from the sensor may result in signaling an actuator to move the piston in response to the occlusion break detection to compensate for a vacuum pressure drop associated with the occlusion break. The handpiece may further include a purge bypass line between the irrigation line and the adjacent line reservoir to allow flow from the irrigation line to travel through the adjacent line reservoir to purge the adjacent line reservoir.

19 Claims, 7 Drawing Sheets

(56) References Cited

U.S. PATENT DOCUMENTS

| | | |
|---|---|---|
| 6,241,700 B1 | 6/2001 | Leukanech |
| 6,287,274 B1 | 9/2001 | Sussman et al. |
| 6,315,755 B1 | 11/2001 | Sussman et al. |
| 6,331,171 B1 | 12/2001 | Cohen |
| 6,398,759 B1 | 6/2002 | Sussman et al. |
| 6,575,929 B2 | 6/2003 | Sussman et al. |
| 6,579,270 B2 | 6/2003 | Sussman et al. |
| 6,589,201 B1 | 7/2003 | Sussman et al. |
| 6,589,204 B1 | 7/2003 | Sussman et al. |
| 6,648,847 B2 | 11/2003 | Sussman et al. |
| 6,676,628 B2 | 1/2004 | Sussman et al. |
| 6,719,011 B2 | 4/2004 | Cull et al. |
| 6,752,795 B2 | 6/2004 | Cull |
| 6,780,166 B2 * | 8/2004 | Kanda et al. .................... 604/31 |
| 6,860,868 B1 | 3/2005 | Sussman et al. |
| 7,083,591 B2 | 8/2006 | Cionni |
| 7,645,256 B2 | 1/2010 | Boukhny |
| 2002/0019607 A1 * | 2/2002 | Bui .................................. 604/67 |
| 2002/0161326 A1 | 10/2002 | Sussman et al. |
| 2004/0077993 A1 | 4/2004 | Cionni |
| 2004/0092800 A1 | 5/2004 | Mackool |
| 2005/0054971 A1 | 3/2005 | Steen et al. |
| 2006/0041220 A1 | 2/2006 | Boukhny |
| 2006/0078448 A1 | 4/2006 | Holden |
| 2006/0161101 A1 | 7/2006 | Dimalanta et al. |
| 2006/0173403 A1 | 8/2006 | Injev |
| 2006/0184091 A1 | 8/2006 | Dimalanta et al. |
| 2006/0224163 A1 | 10/2006 | Sutton |
| 2007/0000301 A1 | 1/2007 | Todd et al. |
| 2008/0188792 A1 | 8/2008 | Barrett |

OTHER PUBLICATIONS

International Searching Authority, International Search Report, PCT/US2010/041786, Oct. 28, 2010, 5 pages.

International Searching Authority, Written Opinion of the International Searching Authority, PCT/US2010/041786, Oct. 28, 2010, 7 pages.

* cited by examiner

PHACOEMULSIFICATION HANDPIECE PRESSURE BOOSTER

FIELD OF THE INVENTION

The present invention generally pertains to ophthalmic surgery. More particularly, but not by way of limitation, the present invention pertains to a pressure booster for a surgical handpiece.

DESCRIPTION OF THE RELATED ART

The human eye in its simplest terms functions to provide vision by transmitting light through a clear outer portion called the cornea, and focusing the image by way of the lens onto the retina. The quality of the focused image depends on many factors including the size and shape of the eye, and the transparency of the cornea and lens.

When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an intraocular lens (IOL).

Cataractous lenses may be removed by a surgical technique called phacoemulsification. The diseased lens, once removed, may be replaced by an artificial lens. During the procedure to remove the lens, a cutting tip on a phacoemulsification handpiece may be inserted into the diseased lens and vibrated ultrasonically. The vibrating cutting tip may liquefy or emulsify the lens so that the lens may be aspirated out of the eye. The material may be aspirated out of the eye through an aspiration port on the end of the phacoemulsification handpiece. Irrigation may also be provided at the end of the phacoemulsification handpiece to assist in removal of the lens material. A dangerous condition can occur if lens material temporarily clogs the aspiration port (or attached aspiration line). During the clog, the vacuum in the aspiration line may build, and when the lens material finally breaks free, the excess vacuum pressure may then aspirate portions of the eye which may cause damage to the eye (e.g., collapse).

SUMMARY OF THE INVENTION

In various embodiments, a handpiece may include a main irrigation line configured to provide fluid to a surgical site and an aspiration line configured to aspirate fluid from the surgical site. The main irrigation line may be coupled to an adjacent line reservoir with a piston configured to move within the adjacent line reservoir to increase an irrigation pressure in the main irrigation line near the surgical site. In some embodiments, a sensor may be used to detect an occlusion break in the aspiration line and information from the sensor may be used to determine when to signal an actuator to move the piston in response to the occlusion break detection to compensate for a vacuum pressure drop associated with the occlusion break. The handpiece may further include a purge bypass line between the irrigation line and the adjacent line reservoir to allow flow from the irrigation line to travel through the adjacent line reservoir. The piston may be withdrawn past an entrance of the purge bypass line while purging the adjacent line reservoir, and the piston may seal an entrance of the purge bypass line to the adjacent line reservoir when the piston is positioned between the entrance and the adjacent line reservoir.

BRIEF DESCRIPTION OF THE DRAWINGS

For a more complete understanding of the present invention, reference is made to the following description taken in conjunction with the accompanying drawings in which.

It is to be understood that both the foregoing general description and the following detailed description are exemplary and explanatory only and are intended to provide a further explanation of the present invention as claimed.

DETAILED DESCRIPTION OF THE EMBODIMENTS

Figure 1:
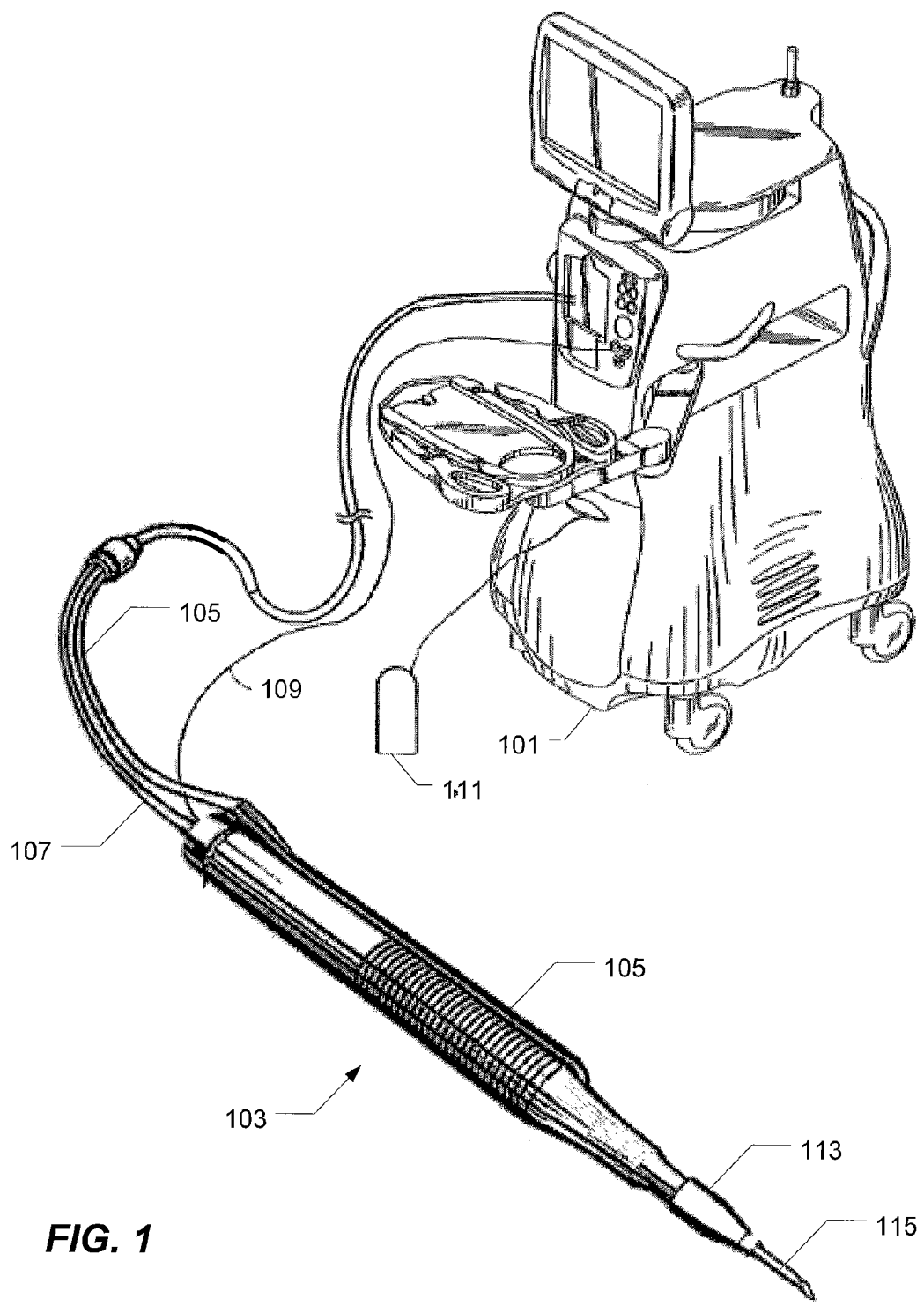
FIG. 1 illustrates a phacoemulsification surgical console connected to a handpiece through an irrigation line and an aspiration line, according to an embodiment.

FIG. 1 illustrates a phacoemulsification surgical console 101 connected to a handpiece 103 through an irrigation line 105 and an aspiration line 107. In some embodiments, power may be supplied to handpiece 103 through electrical cable 109 and flow through lines 105 and 107 may be controlled by a user (e.g., via footswitch 111) to perform a phacoemulsification procedure. In some embodiments, irrigation may be delivered through the tip at an irrigation sleeve 113 at least partially surrounding a cutting tip 115. One example of a handpiece for a phacoemulsification procedure is described in U.S. Patent Application Publication entitled "Ultrasound Handpiece," Publication No. 2006/0041220, Ser. No. 11/183, 591, by Mikhail Boukhny, James Y. Chon, and Ahmad Salehi filed Jul. 18, 2005, which is hereby incorporated by reference in its entirety as though fully and completely set forth herein.

Figure 2:
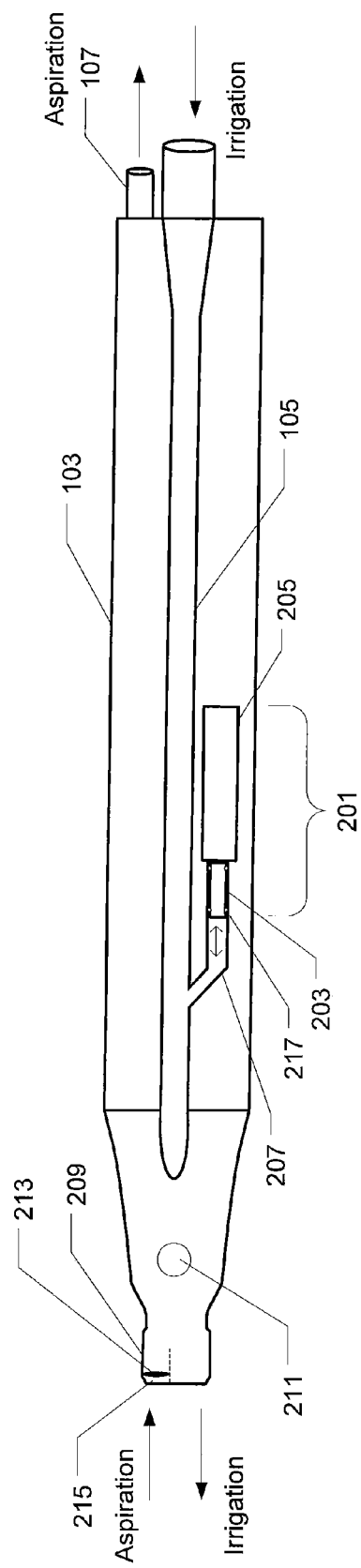
FIG. 2 illustrates a handpiece with an irrigation pressure booster, according to an embodiment.

FIG. 2 illustrates a handpiece 103 with an irrigation pressure booster 201, according to an embodiment. In some embodiments, the irrigation pressure booster 201 may include a piston 203 and an actuator 205. Actuator 205 may include an electro-mechanical linear actuator, a pneumatic cylinder, a solenoid, a spring, etc. Other actuators are also contemplated. Piston 203 may be in an adjacent line reservoir 207 coupled to the main irrigation line 105. Actuator 205 may move piston 203 within the adjacent line reservoir 207 to provide a local increase in pressure in the main irrigation line 105 near the tip 209 of the handpiece 103 (i.e., close to the irrigation site in the eye). The increase in pressure may increase the speed of intraocular pressure (IOP) recovery in the eye after a sudden drop in IOP due to the break-up of an occlusion 213 in the aspiration line 107 (e.g., at aspiration port 215). In some embodiments, a sensor 211 (e.g., non-invasive pressure sensor) may monitor pressures (e.g., in the aspiration line 107 or irrigation line 105). Other sensor types are also contemplated (e.g., a flow rate sensor). In some embodiments, the sensor 211 may be located in the handpiece 103 (e.g., near the tip of the handpiece 103) or in a cassette coupled to the handpiece 103 through the aspiration line 107. Other sensor locations are also possible. In some embodiments, a controller, such as controller 305 as seen in FIG. 3, may use data from the sensor 211 to determine when to trigger the actuator 205 to move the piston 203 (e.g., may trigger the actuator when pressure data or flow rate data indicates a vacuum pressure drop corresponding to an occlusion break in the aspiration line 107).

For example, during aspiration, pressures in the aspiration line 107 may range between approximately +80 mmHg (millimeters of mercury) (positive pressure) to approximately −720 mmHg (vacuum). Other pressures are also contemplated. Flow rates in the aspiration line 107 may vary between approximately 0-60 cc/min (cubic centimeters/minute). Other flow rates are also contemplated. During an occlusion event (e.g., when lens material occludes the aspiration line 107 during a phacoemulsification procedure), flow rates may drop (e.g., to approximately 0 cc/min). When the occlusion breaks, there may be a sudden demand for flow from the eye 303 based on the vacuum level achieved (e.g., in the aspiration line 107) and the compliance of the system (e.g., the compliance of the aspiration line 107). In some embodiments, the level of vacuum achieved in the aspiration line 107 may be limited by the surgical console 101 discontinuing vacuum when the vacuum in, for example, the aspiration line 107 reaches a limit. For example, a surgeon may set a predetermined limit between approximately −300 to −500 mmHg (vacuum) (other limits are also contemplated). Following a pressure decrease (e.g., a pressure decrease detected by the pressure sensor 211 in the aspiration line 107 of, for example, −300 mmHg), the controller 305 may use data from the sensor 211 to determine when the occlusion breaks. For example, when data from the sensor 211 indicates a vacuum pressure drop (e.g., a drop from −300 mmHg to 0 mmHg) or, for example, when data from sensor 211 indicates an increase in flow rate, the controller 305 may actuate the irrigation pressure booster 201 to increase pressure in the irrigation line 105 and supply irrigation fluid to the eye 303 to reduce the amount of material aspirated from the eye 303 during the occlusion break. The sensitivity of the detection may be a default in the system or may be set by the surgeon. For example, the sensitivity may indicate that when a vacuum pressure drop of 200 mmHg is detected, the controller 305 should trigger the irrigation pressure booster 201. Other sensitivities are also contemplated. In some embodiments, detection and/or triggering may be performed by the controller 305 local to the handpiece 103 and/or, for example, a controller on the surgical console 101 that is electrically connected to the sensor 211 and/or controller 305).

Figure 3:
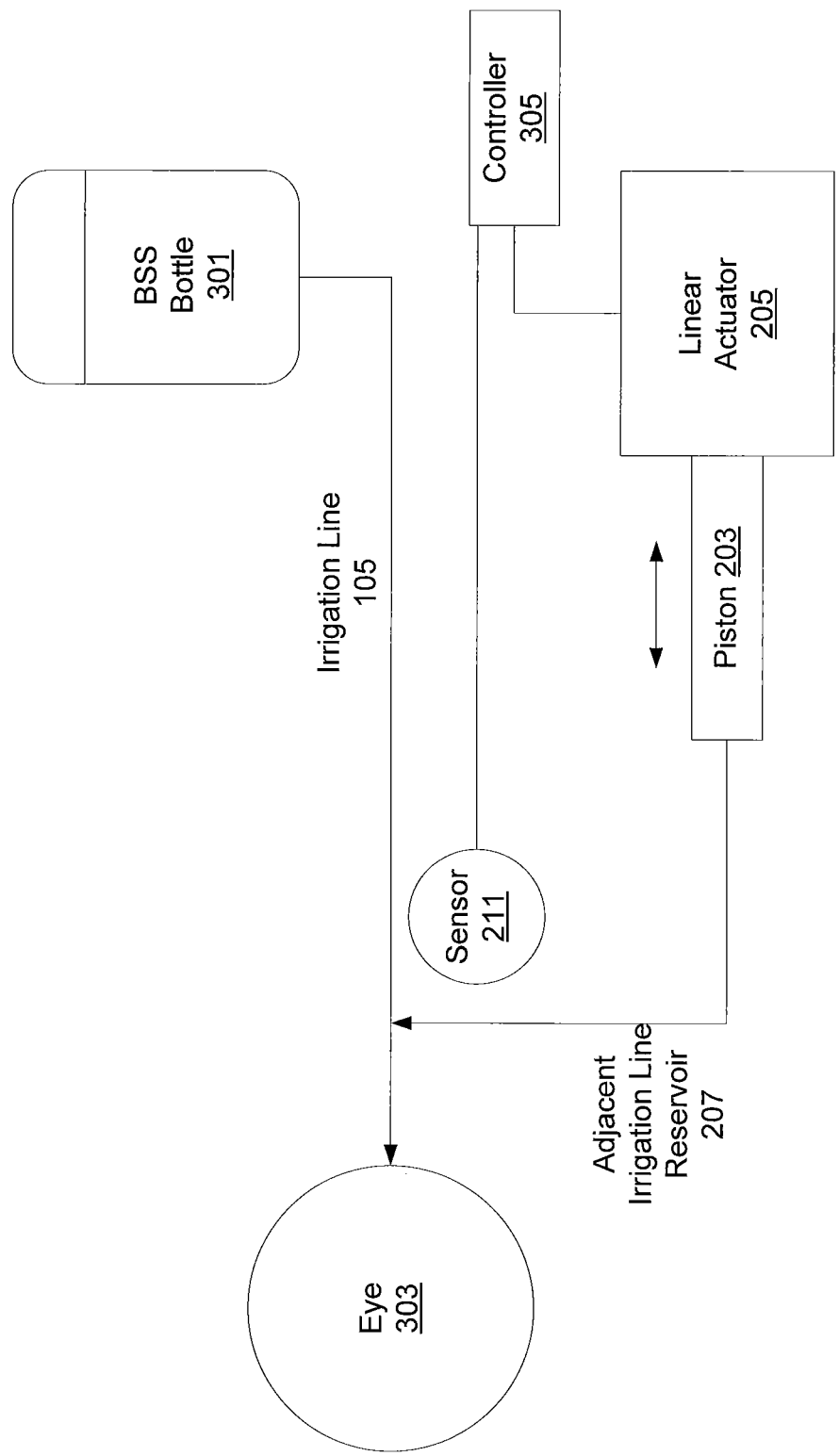
FIG. 3 illustrates a diagram of the irrigation system, according to an embodiment.

FIG. 3 illustrates a diagram of the irrigation system, according to an embodiment. A Balanced Salt Solution (BSS™) may be used as an irrigation source 301. Main irrigation line 105 may operate as the main line between the irrigation source 301 and the eye 303. Actuator 205 (e.g., controlled by controller 305) may move piston 203 to pressurize adjacent irrigation line reservoir 207 coupled to the main irrigation line 105 near the irrigation site at the eye 303. In some embodiments, pressurizing the adjacent irrigation line reservoir 207 may deliver between approximately 0.01 and 0.16 cc to the irrigation line. Other volumes are also contemplated (e.g., 0.15 cc to 3 cc). The volume of BSS™ may be different for different irrigation line 105 or aspiration line 107 dimensions (larger irrigation lines or aspiration lines may need more volume to compensate for the larger fluid volume loss during occlusion). In some embodiments, the irrigation line reservoir 207 may receive BSS™ from the main irrigation line 105 during normal operation of the irrigation line 105. In some embodiments, the piston 203 may include a single piece (e.g., a single piece silicon rubber piston 203) or may include multiple pieces attached to the actuator 205. For example, the piston 203 may include a stainless steel shaft with one or more o-ring seals 217 circumscribing the shaft to form a seal between the piston and the walls of the reservoir 207. Other piston configurations are also possible (e.g., a plastic shaft with a silicone rubber tip or a stainless steel shaft and a soft plastic tip).

Figure 4:
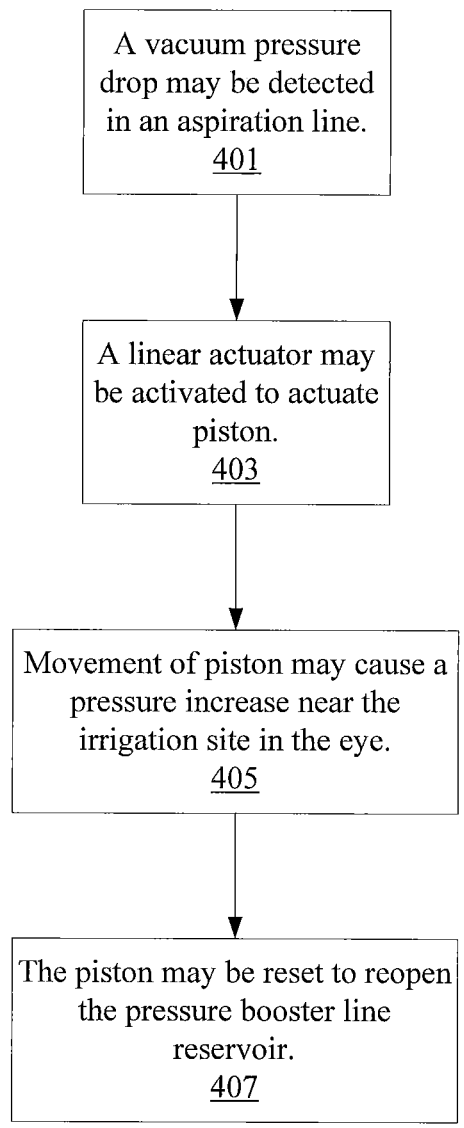
FIG. 4 illustrates a flowchart of an embodiment of a method for providing a pressure boost at an irrigation site.

FIG. 4 illustrates a flowchart of an embodiment of a method for providing a pressure boost at an irrigation site. The elements provided in the flowchart are illustrative only. Various provided elements may be omitted, additional elements may be added, and/or various elements may be performed in a different order than provided below.

At 401, a vacuum pressure drop may be detected in an aspiration line 107 (e.g., caused by a break-up of an occlusion). For example, a sensor 211 in fluid communication with an aspiration line 107 and/or irrigation site at the eye 303 may detect a vacuum pressure drop (or, for example, flow rate change) indicating a breakup of an occlusion. An occlusion 213 may inhibit fluid flow in the aspiration line 107 resulting in a build-up in vacuum. The occlusion may be detected through data from the sensor 211 (e.g., a pressure reading of −300 mmHg to −500 mmHg or a flow rate of 0 cc/min). Following detection of the occlusion, the system (e.g., controller 305) may monitor data from the sensor 211 to determine when the occlusion breaks up. When the occlusion 213 finally breaks up, their may be a sudden inrush of liquid and debris in the aspiration line 107 to equalize the pressure in the aspiration line 107. The sudden inrush of fluid may be detected as a vacuum pressure drop (or flow rate change) by sensor 211 (e.g., the vacuum pressure drop may include a pressure drop from −300 mmHg to 0 mmHg). Other pressure drops are also contemplated.

At 403, actuator 205 may be activated to actuate piston 203 (e.g., by pushing the piston 203). In some embodiments, a controller 305 (e.g., coupled to the sensor 211) may receive the pressure signal and may operate the actuator 205 (e.g., by triggering the actuator 205, powering the actuator 205, etc.) to move the piston 203. In some embodiments, the actuator 205 may respond directly to information from the sensor 211 (e.g., a circuit coupled to the actuator 205 may interpret information from the sensor 211 and may trigger the actuator 205). As another example, the sensor 211 may be programmed to send a signal to the actuator 205 if a vacuum pressure drop of a predetermined magnitude is detected (e.g., 200 mmHg). Other communication configurations for the actuator 205 are also contemplated.

At 405, movement of piston 203 may cause a pressure increase (e.g., in the main irrigation line 105) near the irrigation site in the eye 303. The pressure increase may compensate for the sudden vacuum pressure drop resulting from the occlusion break-up by temporarily supplying additional flow to the main irrigation line 105. Compensating for the sudden vacuum pressure drop may prevent excess fluid from being pulled out of the eye 303 (which could damage the eye) in response to the sudden vacuum pressure drop. A signal from the pressure sensor 211 may also be sent at substantially the same time to a controller (e.g., a closed loop controller or other type of processor) to increase pressure to the irrigation line 105 for longer term compensation. Since a pressure wave travels at the speed of sound from the irrigation reservoir 301 and the pressure booster 201, the increase in pressure from the pressure booster 201 may reach the eye 303 first since the pressure booster 201 is closer. The closer proximity to the eye 303 may therefore have a more immediate effect on the stabilization of IOP. The pressure wave from the irrigation reservoir may then follow to further stabilize the IOP. In some embodiments, the response time of the system (to the vacuum pressure drop) may be approximately 100 ms (approximately 70 ms to detect the vacuum pressure drop and approximately 30 ms to initiate the pressure booster). Other response times, detection times and initiation times are also contemplated.

At 407, the actuator 205 may reset the position of the piston (e.g., pull the piston back to its original location to reopen the line reservoir 207. In some embodiments, the piston may be reset during normal handpiece operation (e.g., when there is a flow of irrigation fluid in the irrigation line 105). As the piston 203 is pulled back, the line reservoir 207 may reopen and refill with irrigation fluid such that the pressure booster will be positioned to respond to another occlusion event.

Figure 5A:
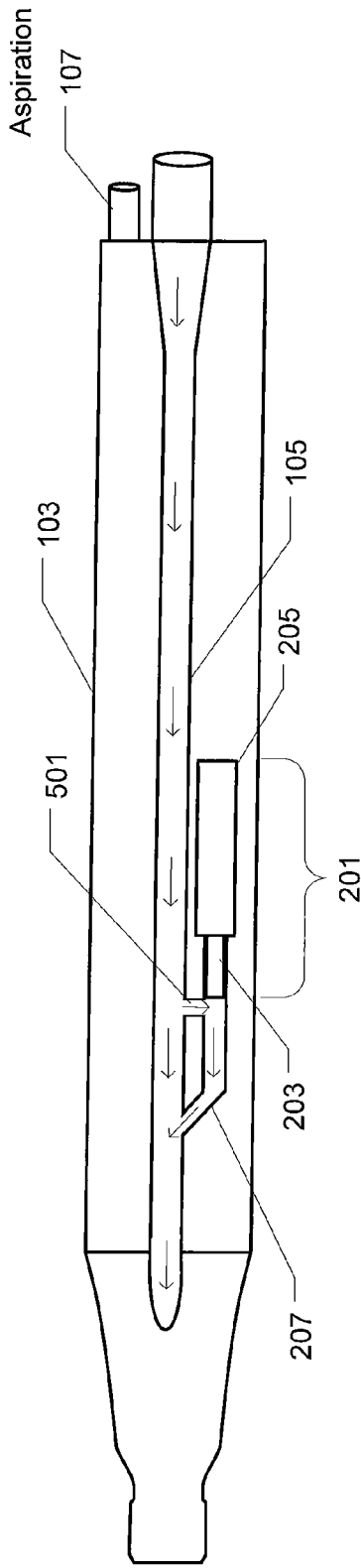
FIGS. 5*a-b* illustrate a purge bypass line, according to an embodiment.
Figure 5B:
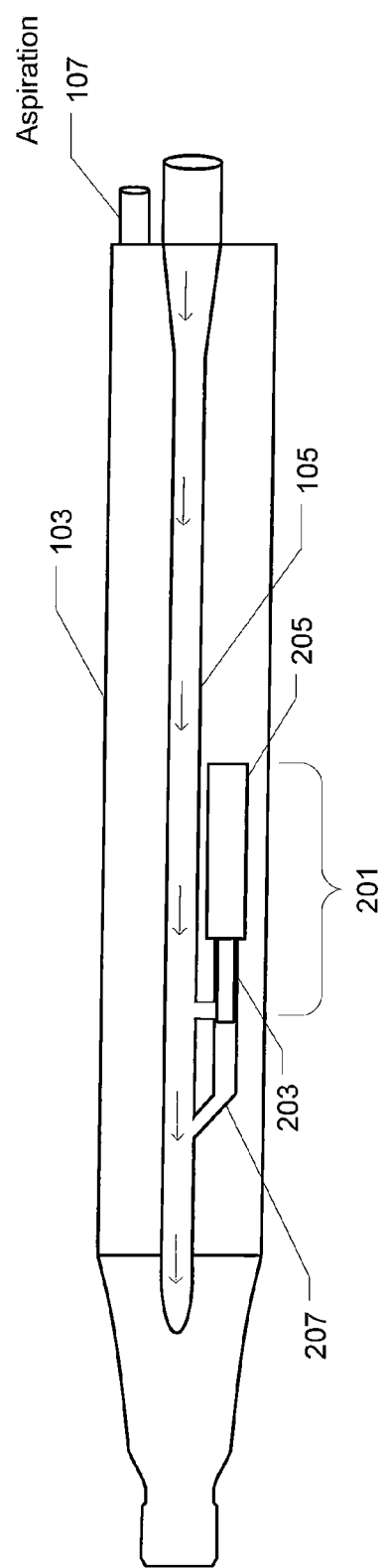
Figure 6:
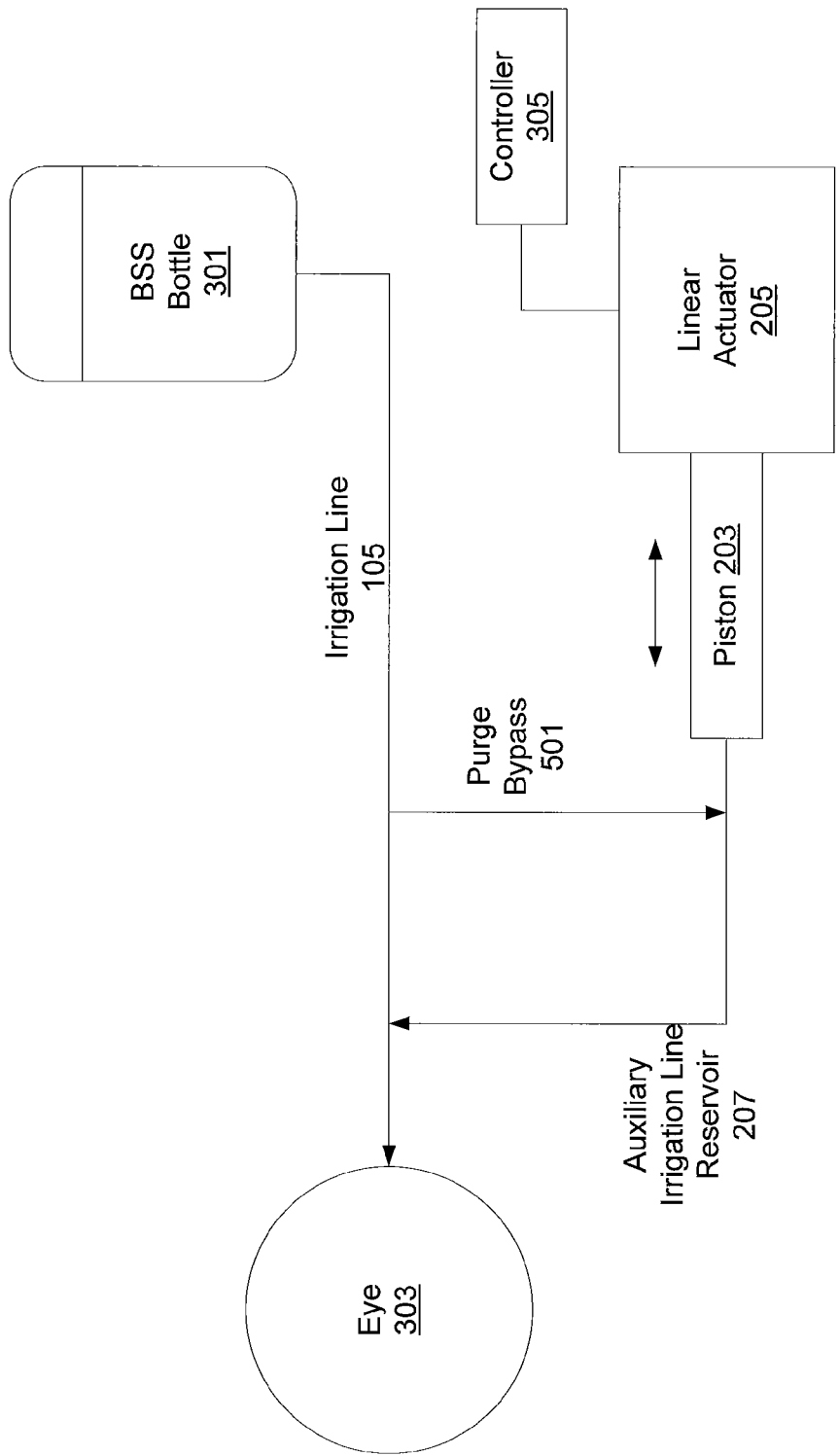
FIG. 6 illustrates a flow diagram including the purge bypass line, according to an embodiment.

FIGS. 5*a-b* illustrate a purge bypass line 501, according to an embodiment. In some embodiments, the purge bypass line 501 may be attached to the main irrigation line 105 ported into the pressure booster line reservoir 207 to allow flow from the main irrigation line 105, through the pressure booster reservoir 207 and back into the main irrigation line 105 to purge air from the system (also see flow diagram in FIG. 6). Air may be purged from the system, for example, before phacoemulsification to prevent/reduce the amount of air pushed into the eye 303 from the irrigation line 105. After the purge, the actuator 205 may drive the piston 203 forward to seal off the purge bypass line 501 (see FIG. 5*b*) and prepare the piston 203 to be pushed forward in response to an occlusion break.

Figure 7:
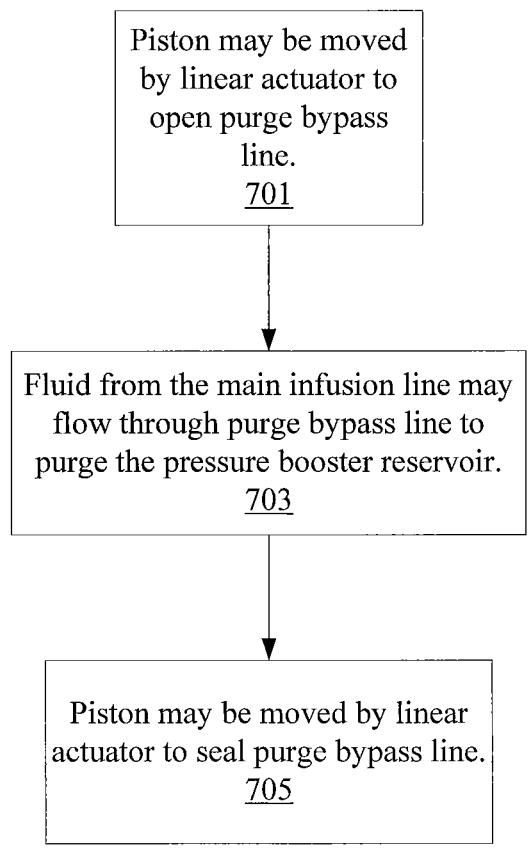
FIG. 7 illustrates a flowchart of an embodiment of a method for purging the purge bypass line.

FIG. 7 illustrates a flowchart of an embodiment of a method for purging the purge bypass line 501. The elements provided in the flowchart are illustrative only. Various provided elements may be omitted, additional elements may be added, and/or various elements may be performed in a different order than provided below.

At 701, piston 203 may be moved by actuator 205 to open purge bypass line 501. In some embodiments, controller 305 may coordinate operation of the actuator 205 and the purge flow through the irrigation line 105.

At 703, fluid from the main irrigation line 105 may flow through purge bypass line 501 to purge the pressure booster reservoir 207.

At 705, piston 203 may be moved by actuator 205 to seal purge bypass line 501. Once sealed, flow through the main irrigation line 105 may flow over, but not through the purge bypass line 501. In this configuration, the piston 203 may be prepared to be pushed forward in response to an occlusion break. In some embodiments, the purge may be performed prior to an ophthalmic procedure (and may not need to be repeated during the procedure).

In some embodiments, the surgical console, handpiece 103, etc. may include one or more processors. The processor may include single processing devices or a plurality of processing devices. Such a processing device may be a microprocessor, controller (e.g., controller 305) (which may be a micro-controller), digital signal processor, microcomputer, central processing unit, field programmable gate array, programmable logic device, state machine, logic circuitry, control circuitry, analog circuitry, digital circuitry, and/or any device that manipulates signals (analog and/or digital) based on operational instructions. The memory coupled to and/or embedded in the processors may be a single memory device or a plurality of memory devices. Such a memory device may be a read-only memory, random access memory, volatile memory, non-volatile memory, static memory, dynamic memory, flash memory, cache memory, and/or any device that stores digital information. Note that when the processors implement one or more of its functions via a state machine, analog circuitry, digital circuitry, and/or logic circuitry, the memory storing the corresponding operational instructions may be embedded within, or external to, the circuitry comprising the state machine, analog circuitry, digital circuitry, and/or logic circuitry. The memory may store, and the processor may execute, operational instructions corresponding to at least some of the elements illustrated and described in association with, for example, FIGS. 4 and 7.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A handpiece, comprising:
a main irrigation line configured to provide fluid to a surgical site;
an aspiration line configured to aspirate fluid from the surgical site;
an adjacent line reservoir, in the handpiece, fluidly coupled to and branching from the main irrigation line in the handpiece;
a piston configured to move within the adjacent line reservoir such that motion of the piston toward the main irrigation line pushes fluid out of the adjacent line reservoir and into the main irrigation line;
a sensor, wherein data from the sensor is used to detect an occlusion break in the aspiration line; and
an actuator configured to move the piston in response to the occlusion break detection, wherein moving the piston in the adjacent line reservoir increases an irrigation flow to compensate for a vacuum pressure drop associated with the occlusion break.

2. The handpiece of claim 1, further comprising a purge bypass line between the main irrigation line and the adjacent line reservoir, wherein the purge bypass line is configured to allow flow from the main irrigation line to travel through the adjacent line reservoir, when the piston is withdrawn past an entrance of the purge bypass line, to purge the adjacent line reservoir.

3. The handpiece of claim 2, wherein the piston is configured to seal an entrance of the purge bypass line to the adjacent line reservoir when the piston is positioned between the entrance and the adjacent line reservoir.

4. The handpiece of claim 1, wherein the actuator is an electro-mechanical linear actuator, a pneumatic cylinder, a solenoid, or a spring.

5. The handpiece of claim 1, wherein the sensor is a pressure sensor and wherein detecting an occlusion break in the aspiration line comprises detecting a vacuum pressure drop in the aspiration line below a predetermined threshold.

6. The handpiece of claim 1, wherein the sensor is a pressure sensor and wherein detecting an occlusion break in the aspiration line comprises detecting a vacuum pressure drop in the aspiration line after a pressure of approximately −300 mmHg to −500 mmHg is detected in the aspiration line.

7. The handpiece of claim 1, wherein the sensor is a flow rate sensor and wherein detecting an occlusion break in the aspiration line comprises detecting a change in flow rate in the aspiration line after a flow rate of approximately 0 cc/min is detected.

8. The handpiece of claim 1, wherein the piston is configured to push fluid out of the adjacent line reservoir directly into the main irrigation line.

9. The handpiece of claim 1, wherein the piston is configured to push fluid out of the adjacent line reservoir into the main irrigation line such that the fluid from the adjacent line reservoir enters the main irrigation line prior to entering the aspiration line.

10. A method, comprising:
providing fluid to a surgical site in an eye through a main irrigation line of a handpiece;
aspirating fluid from the surgical site through an aspiration line of the handpiece;
detecting a vacuum pressure drop in the aspiration line of the handpiece; and
pushing fluid out of an adjacent irrigation line reservoir in the handpiece and into the main irrigation line of the handpiece by actuating a piston in the adjacent irrigation line reservoir to cause a pressure increase near the surgical site in the eye.

11. The method of claim 10, further comprising purging the adjacent line reservoir through a purge bypass line between the main irrigation line and the adjacent line reservoir, wherein the purge bypass line is configured to allow flow from the main irrigation line to travel through the adjacent line reservoir, when the piston is withdrawn past an entrance of the purge bypass line, to purge the adjacent line reservoir.

12. The method of claim 11, wherein the piston is configured to seal an entrance of the purge bypass line to the adjacent line reservoir when the piston is positioned between the entrance and the adjacent line reservoir.

13. The method of claim 10, wherein actuating the piston comprises using an electro-mechanical linear actuator, a pneumatic cylinder, a solenoid, or a spring.

14. The method of claim 10, wherein pushing fluid out of the adjacent irrigation line reservoir comprises sending a signal to an actuator controlling the piston and wherein the method further comprises sending a separate signal to increase pressure in the irrigation pressure line for longer term compensation.

15. The method of claim 10, wherein the piston is actuated when a vacuum pressure drop in the aspiration line corresponding to an occlusion break is detected.

16. The method of claim 15, wherein detecting the occlusion break comprises detecting a vacuum pressure drop in the aspiration line through a pressure sensor configured to monitor a pressure of fluid in the aspiration line.

17. The method of claim 16, wherein detecting the occlusion break comprises detecting a vacuum pressure drop in the aspiration line after a pressure of approximately −300 mmHg to −500 mmHg is detected in the aspiration line.

18. The method of claim 16, wherein the vacuum pressure drop comprises a change in pressure from approximately between −300 mmHg and −500 mmHg down to approximately 0 mmHg.

19. The method of claim 15, wherein detecting the occlusion break comprises detecting a change in flow rate in the aspiration line, through a flow rate sensor configured to monitor a flow rate of fluid in the aspiration line, after a flow rate of approximately 0 cc/min is detected.

* * * * *